United States Patent [19]

Engels et al.

[11] 4,006,186
[45] Feb. 1, 1977

[54] PROCESS FOR THE PREPARATION OF THIOPHENOLS

[75] Inventors: Hans Dieter Engels, Solingen; Rolf-Jürgen Singer, Wuppertal-Vohwinkel, both of Germany

[73] Assignee: Bayer Aktiengesellschaft, Leverkusen, Germany

[22] Filed: May 2, 1974

[21] Appl. No.: 466,312

Related U.S. Application Data

[63] Continuation of Ser. No. 240,845, April 3, 1972, abandoned.

[30] Foreign Application Priority Data

Apr. 7, 1971 Germany .......................... 2116978

[52] U.S. Cl. .................. 260/577; 260/578; 260/608; 260/609 R; 260/609 D; 260/609 E; 260/609 F; 260/556 H
[51] Int. Cl.² .............. C07C 149/00; C07C 149/12
[58] Field of Search .............. 260/577, 578, 609 R, 260/608, 556 H

[56] References Cited

UNITED STATES PATENTS

| | | | |
|---|---|---|---|
| 3,331,205 | 7/1967 | Laufer | 260/608 |
| 3,459,813 | 8/1969 | Dombro | 260/608 |

FOREIGN PATENTS OR APPLICATIONS 1,518,105  1/1969  Germany

OTHER PUBLICATIONS

Houben–Weyl, "Methodender Organishem Chemie," 4th Ed., vol. 9, pp. 29–31, 70–73, 77, 78, 648–652.
Kubota et al., Chemical Abstracts, 1961, col. 19925.
Foss et al., J. Am. Chem. Soc. 60, (1938), pp. 2729–2730.

*Primary Examiner*—Arthur P. Demers
*Attorney, Agent, or Firm*—Burgess, Dinklage & Sprung

[57] ABSTRACT

Process for the production of thiophenols of the formula

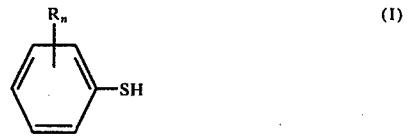

in which
 n is an integer from 0 to 5, inclusive, and
 R is hydroxy, nitro, halogen, alkyl of from 1 to 6 carbon atoms, alkoxy of from 1 to 6 carbon atoms, amino, monoalkylamino or dialkylamino.

which process comprises reacting, in a first step, the corresponding phenylsulfonic acid chloride with hydrazine, hydriodic acid and hydrochloric acid to give the corresponding sulfonehydrazide; and reacting the product so formed, in the second step, to give the corresponding disulfide; and then splitting the resulting material, in the third step, with hydrazine and alkali to form a thiophenolate from which the thiophenol can be liberated by treatment with a mineral acid.

21 Claims, No Drawings

PROCESS FOR THE PREPARATION OF THIOPHENOLS

This is a continuation of application Ser. No. 240,845, filed Apr. 3, 1972, now abandoned The present invention relates to a novel process for the preparation of certain known thiophenols compounds. Such compounds are used as polymerization inhibitors and antioxidants as well as intermediates for the preparation of dyestuffs and cropprotection agents.

It is known that thiophenols are obtained when phenylsulfonic acid chlorides are reduced with hydrazine at high temperatures to give the disulfides, or when phenylsulfonic acid chlorides are reduced with zinc dust in glacial acetic acid with addition of a small amount of concentrated hydrochloric acid, or with zinc dust in sulfuric acid at 0° C, to give the disulfides (see Journal of the Pharmaceutical Society of Japan 81 (1961), No. 4, pages 502–506; Journal of the Chemical Society 123, 2384 (1923); Acta Chimica Acad. Sci. Hung. 1, 319 (1951); Chemisches Zentralblatt 1952, 6199). These disulfides, are converted, by reductive splitting, into the corresponding thiophenols. A disulfide splitting with hydrazine in the presence of pyridine has also been described, in German Published Specification (DOS) 1,518,105. A more practicable method of splitting is catalytic hydrogenation, particularly with Raney nickel as taught by published Dutch Patent Application No. 69,06280.

Industrial processes which lead directly from the sylfochlorides to the thiophenols are those using zinc and hydrochloric acid (see Journal fuer praktische Chemie (2) 29, 376 (1884); Houben-Weyl, Methoden der Organischen Chemie, Volume 9, page 23), or the process with red phosphorus and hydriodic acid (see Bulletin de la Soc. chim. de France, 1962, No. 3, pages 502–505; U.S. Pat. No. 2,947,788; Journal of the Pharmaceutical Society of Japan 77, 959; Helvetica chimica Acta 22, 601; Berichte der Deutschen Chemischen Gesellschaft 99, 375). These processes, however, exhibit a number of disadvantages. Thus, the reaction of phenylsulfonic acid chloride with hydrazine to give the disulfide proceeds only at very high temperatures. The other methods mentioned for disulfide preparation and splitting are industrial processes which in most cases give thiophenols in good yields but exhibit other sections disadvantages. In the method using zinc and hydrochloric acid, the waste-water problem and the troublesome evolution of hydrogen gas come to the fore, while, in the Raney nickel splitting, in the first place large amounts of catalyst are necessary since the catalyst becomes poisoned in use, and secondly the method is only restrictedly usable since halogen atoms on the phenyl radical are also split off. In the last-mentioned method, that is the reductive splitting with red phosphorus and hydriodic acid, there arise corrosion problems; it has also been found that this method, too, is only restrictedly usable. Thus, the splitting fails when several halogen atoms are contained in the phenyl nucleus. Working with sizeable amounts of phosphorus is moreover to be rejected for reasons of works safety.

The present process provides a thiophenol of the formula

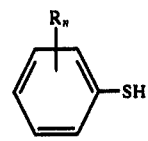  (I)

in which
 n is an integer from 0 to 5, inclusive, and
 R is hydroxy, nitro, halogen, alkyl of from 1 to 6 carbon atoms, alkoxy of from 1 to 6 carbon atoms, amino, monoalkylamino or dialkylamino, wherein each alkyl is of, e.g., 1 to 6 carbon atoms, the radicals R being identical or different when n is from 2 to 5; optionally in the form of a corresponding thiophenolate.

In the formula (II), n stands preferably for 0, 1 or 2; and each R is chlorine, bromine, hydroxy, amino, alkyl, of from 1 to 4 carbon atoms, alkoxy of from 1 to 4 carbon atoms, methylamino, ethylamino, n- or isopropylamino or dimethyl-, diethyl-, di-n-propyl-, di-isopropyl-, methyl-ethyl-, methyl-n-propyl-, methyl-isopropyl-, ethyl-n-propyl- or ethyl-isopropylamino.

Essentially, the instant process comprises reacting, in a first step, a phenylsulfonic acid chloride of the formula

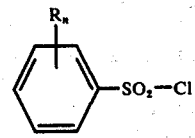  (II)

(in which R and n are defined as above)
with hydrazine, hydriodic acid and hydrochloric acid at a temperature of from 0° to 40° C to give the corresponding sulfonehydrazide; and reacting the product so formed, in a second step, at from 60° to 120° C to give the corresponding disulfide; the latter material, in a third step, is split with hydrazine and alkali at a temperature of from 60° to 120° C in a solvent to form a thiophenolate, the thiophenol being liberated therefrom, if required, with a mineral acid.

By this process the thiophenols of the formula (I) may be prepared in high purity and in good yield.

The process according to the present invention exhibits a number of advantages. First is its simple industrial feasibility with low expenditure of apparatus. Furthermore, in contrast to the above-mentioned prior-art processes, no waste-water or corrosion problems arise. The resultant thio-phenols do not have to be worked up by distillation and are obtained in high purity. Moreover, the general practicability of the process is a particular advantage.

If phenylsulfonic acid chloride and hydrazine are used as starting materials, the reaction course can be represented by the following equations:

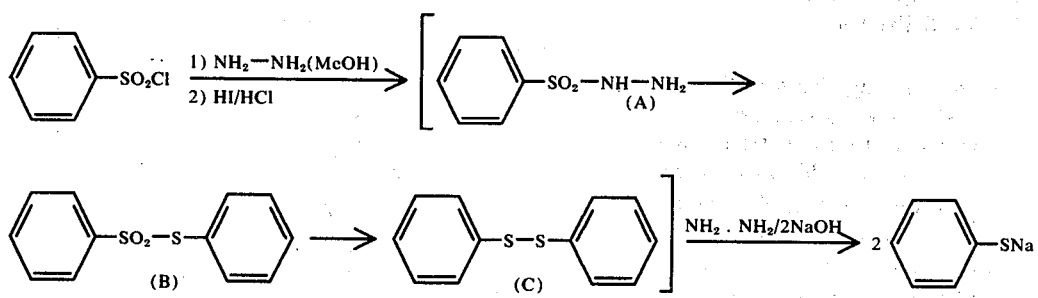

An isolation of the intermediate compounds (A), (B) and (C) is for practical reasons not normally effected.

During the course of the reactions, reactive groups R may be protected by methods known in the art; in particular hydroxyl, amino and monoalkylamino groups may be first acylated and, after the formation of the thiophenolate or thiophenol, restored.

As examples of the phenylsulfonic acid chlorides which can be used according to the invention, there are mentioned: 2-chloro-, 3-chloro-, 4-chloro-, 2-bromo-, 3-bromo-, 4-bromo-, 2,5-dichloro-, 3,4-dichloro-, 2-methyl-, 2-ethyl-, 2-isopropyl-, 2-n-propyl-, 2-n-butyl-, 2-sec.-butyl-, 2-tert.-butyl-, 2-isobutyl-, 4-methyl-, 4-ethyl-, 4-isopropyl-, 4-n-propyl-, 4-n-butyl-, 4-isobutyl-, 4-tert.-butyl-, and 4-sec.-butylphenylsulfonic acid chlorides; 4-hydroxy- and 4-aminophenylsulfonic acid chlorides, preferably with an acyl protective group; and 4-dimethyl-, 4-diethyl-, 4-di-n-propyl-, 4-di-n-butyl-, 4-di-tert.-butyl-, 4-methyl-, 4-ethyl-, 4-n-propyl-, 4-iso-propyl-, 4-methylethyl-, 4-methylpropyl- and 4-ethylpropylaminophenylsulfonic acid chlorides.

The phenylsulfonic acid chlorides to be used as starting materials are known and can be prepared according to processes described in the literature.

As a solvent or diluent for the process, an inert organic solvent or diluent is suitable, especially an alcohol, such as methanol, ethanol or isopropanol; aqueous alcohols also constitute preferred solvents.

The reaction temperatures can be varied within a fairly wide range: the reaction in the first step is carried out at from 0° to 40° C, preferably from 10° to 30° C, and the reactions in the second step and in the third step are effected at from 60° to 120° C, preferably at from 60° to 80° C.

The reaction is, in general, carried out at normal pressure.

A preferred mode of carrying out the process according to this invention is as follows. The sulfochloride (II) and hydrazine hydrate are reacted, in a molar ratio of 1:3 respectively, at from 15° to 20° C in the solvent stated in Example 1 hereinafter. After brief subsequent stirring, hydriodic acid and then hydrochloric acid are added and the mixture is heated under reflux for 2 to 4 hours. After cooling the mixture to 20° C, water is added, say in an amount of 1 liter per mole of starting sulfochloride (II). The precipitated disulfide is not isolated, nor are the sulfone hydrazide (for example compound (A)) and the sulfonic acid thiol ester (for example compound (B)) isolated. However, it has been found that these two last-mentioned compounds can, however, be isolated. The disulfide is now heated under reflux for one to several hours with alkali (especially sodium hydroxide solution) and hydrazine hydrate in the molar ratio 1:2–3:2–5 in an alcoholic-aqueous medium until a clear solution has formed; thereafter, concentration is effected in a vacuum, and water is subsequently added. After acidification with hydrochloric acid, the precipitated thiophenol is separated and washed with water.

If the thiophenol is not required in a free form for further reaction, the acidification can also be dispensed with and the thiophenolate solution be further reacted directly.

The following Examples illustrate the process according to the present invention.

EXAMPLE 1

Preparation of 4 - chlorothiophenol

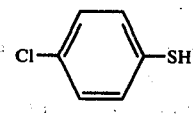

1 mole of 4-chlorophenyl-sulfochloride was dissolved in 600 ml methanol, and 3 moles of hydrazine hydrate were added dropwise in the course of about 45 minutes, with vigorous stirring, the internal temperature being kept at 10° to 20° C by ice cooling. After completion of the addition, stirring was effected for 20 minutes while heating to 30° to 35° C internal temperature. After addition of 5 to 6 g of 57%-strength hydriodic acid, neutralization was effected with concentrated hydrochloric acid. A further 50 to 60 ml of concentrated hydrochloric acid were added, and heating under reflux was subsequently effected for 4 to 5 hours. Neutralization was then effected with a 45%-strength of sodium hydroxide, and 2 moles of hydrazine hydrate and a further 2.5 moles of sodium hydroxide (NaOH), dissolved in 150 ml of water and 200 ml of methanol, were added. After 3 hours' boiling under reflux, the reduction was complete; a colorless solution had formed which upon addition of water showed no or only slight turbidity. The bulk of the methanol used was distilled off at a bath temperature of 130° to 140° C, the residue was diluted with 800 ml of water and adjusted to a pH value of 1 with concentrated hydrochloric acid. The precipitated 4-chlorothiophenol of the melting point 50° to 51° C was obtained in 92% yield.

When liquid thiophenols were prepared, these were separated in liquid form or taken up in a suitable solvent.

In a manner analogous to that above, the following thiophenols can be prepared:

| Example No. | Constitution | Physical properties | Yield in % of the theory |
|---|---|---|---|
| 2 | ⌬—SH | b.p. 77° C/30 mmHg | 90 |
| 3 | CH₃—⌬—SH | m.p. 40° C | 81 |
| 4 | tert.-C₄H₉—⌬—SH | b.p. 115° C/10 mmHg | 91 |
| 5 | Cl—⌬(NH₂)—SH | m.p. 192° C | 83 |
| 6 | HO—⌬—SH | m.p. 29–31° C | 75 |
| 7 | Br—⌬—SH | m.p. 70° C | 83 |
| 8 | H₂N—⌬—SH | m.p. 43° C | 78 |

It will be understood that the specification and examples are illustrative but not limitative of the present invention and that other embodiments within the spirit and scope of the invention will suggest themselves to those skilled in the art.

What is claimed is:

1. A process for the production of a thiophenolate of the formula

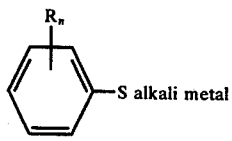

in which
n is an integer from 0 to 5, inclusive, and
R is hydroxy, nitro, halogen, alkyl of from 1 to 6 carbon atoms, alkoxy of from 1 to 6 carbon atoms, amino, monoalkylamino or dialkylamino, wherein each alkyl is of from 1 to 6 carbon atoms, the radicals R being identical or different when n is from 2 to 5;

which consists essentially of the steps of:
i. contacting a phenylsulfonic acid chloride of the formula

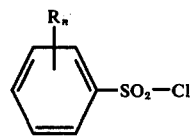

in which R and n are defined as above with hydrazine in a reaction vessel and maintaining the resultant mixture at a temperature of 0° to 40° C;
ii. adding to said mixture in said reaction vessel hydriodic acid and hydrochloric acid and thereafter maintaining the reaction mixture at a temperature of 60°–120° C;
iii. thereafter neutralizing any acid in said reaction mixture by addition of an alkali; and
iv. adding to the so neutralized reaction mixture additional hydrazine and an alkali so that the mol ratio of disulfide in the reaction mixture to alkali to hydrazine is 1:2–3:2–5 and maintaining the reaction mixture for several hours at 60° to 120° C until thiophenolate is formed.

2. Process as claimed in claim 1 wherein said thiophenolate is recovered without subsequent conversion to thiophenol.

3. Process as claimed in claim 1 wherein all the steps are effected in the presence of a solvent comprising an alcohol.

4. Process as claimed in claim 3 wherein said alcohol is an aqueous alcohol.

5. Process as claimed in claim 1 wherein the said first step is carried out at a temperature of from 10° to 30° C., 6. Process as claimed in claim 1 wherein said second step is carried out at a temperature of from 60° to 80° C.

7. Process as claimed in claim 1 wherein the fourth step is carried out at a temperature of from 60° to 80° C.

8. Process as claimed in claim 1 wherein said phenylsulfonic acid chloride and said hydrazine are reacted in a molar ratio of about 1:3.

9. Process as claimed in claim 1 wherein said alkali is sodium hydroxide.

10. Process as claimed in claim 1 wherein the said hydrazine is in the form of hydrazine hydrate.

11. Process as claimed in claim 1 wherein $n$ in formula II is 0, 1 or 2.

12. Process as claimed in claim 1 wherein R in the formulas is hydroxy, nitro or halogen.

13. Process as claimed in claim 1 wherein R in the formulas is alkyl or alkoxy of from 1 to 6 carbon atoms.

14. Process as claimed in claim 1 wherein R in the formulas is amino, monoalkylamino or dialkylamino and each alkyl is of from 1 to 6 carbon atoms.

15. Process as claimed in claim 1 wherein R in the formulas is chlorine, bromine, hydroxy, amino, alkyl of from 1 to 4 carbon atoms, alkoxy of from 1 to 4 carbon atoms, methylamino, ethylamino, n- or isopropylamino or dimethyl-, diethyl-, di-n-propyl-, di-isopropyl-, methylethyl-, methyl-n-propyl-, methyl-isopropyl-, ethyl-n-propyl- or ethyl-isopropylamino.

16. A process according to claim 1 wherein steps (ii), (iii) and (iv) are performed without any prior separation of intermediate product.

17. A process according to claim 16 wherein following step (iv) without any separation of thiophenolate there is added to the resultant reaction mixture a mineral acid whereby to prepare the corresponding thiophenol.

18. A process according to claim 16 wherein the hydrazine in step (i) is dissolved in a solvent.

19. A process according to claim 18 wherein step (ii) is carried out by heating the reaction mixture at reflux for 2 to 4 hours.

20. A process according to claim 19 wherein step (iv) is performed in an alcoholic-aqueous medium until a clear solution is formed.

21. A process according to claim 17 wherein said mineral acid is hydrochloric acid.

* * * * *

UNITED STATES PATENT AND TRADEMARK OFFICE
CERTIFICATE OF CORRECTION

PATENT NO. : 4,006,186
DATED : February 1, 1977
INVENTOR(S) : Hans Dieter Engels et al It is certified that error appears in the above—identified patent and that said Letters Patent are hereby corrected as shown below:

Column 1, line 36, "sylfochlorides" should read -- sulfochlorides --

1, line 37, "fuer" should read -- für --.

1, lines 53-54, "sections" should read -- serious --.

7, line 5, "C.," should read -- C. --.

Signed and Sealed this

Twenty-fourth Day of May 1977

[SEAL]

Attest:

RUTH C. MASON
Attesting Officer

C. MARSHALL DANN
Commissioner of Patents and Trademarks